United States Patent [19]

Murray et al.

[11] 4,077,409

[45] Mar. 7, 1978

[54] ENCAPSULATED CATAMENIAL DEVICE

[76] Inventors: Jerome L. Murray, 652 First Ave., New York, N.Y. 10016; Frances R. Gardiner, 43 Park Rd., Sparta, N.J. 07871

[21] Appl. No.: 575,201

[22] Filed: May 7, 1975

Related U.S. Application Data

[63] Continuation-in-part of Ser. No. 436,391, Jan. 24, 1974, abandoned.

[51] Int. Cl.$^2$ ............................................. A61F 13/20
[52] U.S. Cl. .................................................... 128/285
[58] Field of Search ............... 128/270, 263, 284, 285, 128/296; 19/144.5

[56] References Cited

U.S. PATENT DOCUMENTS

| | | | |
|---|---|---|---|
| 1,575,123 | 3/1926 | Martocci-Pisculli | 128/270 |
| 2,386,590 | 10/1945 | Calhoun | 128/270 |
| 2,808,832 | 10/1957 | Myers et al. | 128/285 |
| 3,306,966 | 2/1969 | Matejcek et al. | 128/285 |
| 3,595,236 | 7/1971 | Corrigan et al. | 128/285 |
| 3,690,321 | 9/1972 | Hirschman | 128/285 |
| 3,830,236 | 8/1974 | Hanke | 128/270 |

Primary Examiner—Stephen C. Pellegrino
Assistant Examiner—Henry S. Layton
Attorney, Agent, or Firm—Mel K. Silverman; David A. Jackson

[57] ABSTRACT

A catamenial device such as a tampon which comprises a segment of a rapidly reexpandable hydrophilic polymeric foam held in compression to less than 50 percent of its original dry volume and a constraining means holding said segment in compression which is adapted to provide lubrication for insertion of said segment into an animal's body cavity and to thereafter rapidly disintegrate, wherein said constraining means comprises a capsule possessing a plurality of perforations distributed about its surface to hasten disintegration. The devices of the present invention may be stored over an extended period of time without the difficulty of premature escape of the segment from the capsule.

11 Claims, 5 Drawing Figures

ENCAPSULATED CATAMENIAL DEVICE

CROSS REFERENCE TO RELATED APPLICATIONS

This application is a continuation-in-part of co-pending Ser. No. 436,391 filed on Jan. 24, and now abandoned 1974, by the inventors herein.

BACKGROUND OF THE INVENTION

This invention generally relates to catamenial devices such as tampons and other insertable articles which are prepared from hydrophilic polymeric foam materials.

As noted in the above-identified co-pending application, catamenial devices such as tampons have been prepared from a wide variety of synthetic and naturally occuring organic materials in the form of fibers and sponge-like materials, but have all suffered from various critical defects. Generally, a device such as a tampon which is to be inserted in an easily irritable area of the body cavity must possess a refined texture and flexibility, while, at the same time, possessing a significant absorptive capacity and the ability to rapidly and uniformly re-expand in contact with moisture such as occasioned by the menstrual flow. The latter property is required because the device must assume a reduced size to facilitate its insertion.

Generally, prior art devices have lacked one or more of the above properties, as absorption is usually gained at the expense of size, and flexibility and texture are sacrificed to the ability to undergo re-expansion.

In the context of the above discussion, Applicants sought to provide a device combining all of the favorable characteristics, and, accordingly, developed a catamenial device prepared from a hydrophilic, rapidly re-expandable polymeric foam which is compressed to less than 50 percent of its dry volume and then placed within a soluble, lubricious constraining means such as a capsule. The foam possesses the desired texture and provides faultless continual absorption lasting up to 12 hours when a segment is employed with over all dimensions of 1 inch × 1 inch × 2¼ inches.

Further experimentation conducted since the development of the above device has uncovered a useful variation of the constraining means which is believed to provide enhanced re-expansion of the foam.

SUMMARY OF THE INVENTION

In accordance with the present invention, a catamenial device is disclosed which comprises a rapidly expandable hydrophilic polymeric foam compressed and placed within a soluble lubricious constraining means, such as a capsule wherein the constraining means is provided with a perforated surface serving to hasten escape of the foam therefrom in the body cavity. In one embodiment, the perforations may comprise radially intersecting slits originating at the rounded tip portion of the capsule and longitudinally extending substantially the entire length thereof. In another embodiment, the perforations comprise a plurality of pin holes uniformly dispersed primarily about the tip area.

Catamenial devices employing capsules modified in this manner are capable of increased speed of re-expansion and activation in use. In the case of tampons, the incidence of faults such as "by-pass" is virtually eliminated, as the improved expansion of the foam prevents even minor leakage from occurring.

The devices of this invention are easily manufactured by a variety of techniques. The perforations are of such design that the structures are self-sustaining and are capable of constraining the compressed foam for extended periods of time without collapse.

Accordingly, it is a principal object of the present invention to prepare a catamenial device comprising a compressed hydrophilic polymeric foam constrained within a soluble container, which exhibits increased speed of re-expansion in contact with moisture.

It is a further object of the present invention to provide a device as aforesaid wherein said container is perforated over a portion of its surface to hasten disintegration in contact with liquid.

It is yet a further object of the present invention to provide a device as aforesaid which is easily manufactured and possesses extended shelf-life and structural integrity.

Other objects and advantages will be apparent to those skilled in the art from the ensuing description and accompanying drawings.

DETAILED DESCRIPTION

Figure 1:
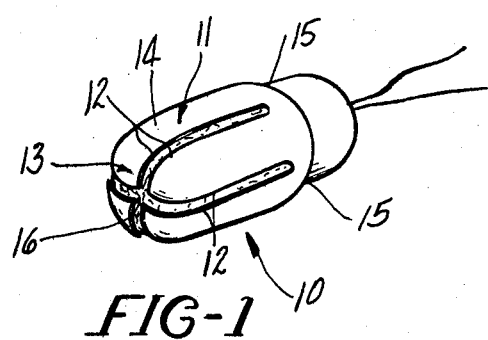
FIG. 1 is a perspective view showing a tampon prepared in accordance with the invention.

In accordance with the present invention, the foregoing objects and advantages are readily obtained.

The present invention comprises a catamenial device prepared from a rapidly reexpandable hydrophilic polymeric foam which is compressed and situated within a soluble lubricious constraining means, which comprises a capsule provided with a perforated outer surface. Specifically, a plurality of perforations is distributed about the capsule's surface which may comprise radially intersecting slits originating at the tip portion of the capsule and longitudinally extending substantially the entire length thereof. In an alternate embodiment, the perforations comprise a plurality of pin holes uniformly dispersed about the tip portion of the capsule.

The preparation of the device of the present invention is generally disclosed in our parent application Ser. No. 436,391. The foams disclosed therein comprise hydrophilic polyurethane foams or hydrophilic formaldehyde polyvinylalcohol foams. It is preferred, however, that the foam be a hydrophilic polyurethane foam. A commercially available hydrophilic polyurethane foam is marketed under the tradename Acquell ® and is available from the Scott Paper Company. This is a polyurethane foam produced by the reaction of a polyesterdiol and tolylene diisocyanate. The polyesterdiol also contains adipic acid and block copolymers of polyoxyethylene and polyoxypropylene.

Another foam which may be used in accordance with this invention is prepared by, in a first step, forming a prepolymer by the reaction of polyethylene glycol and trimethylol propane in a mole ratio of about 2:0.125 to 2:2 respectively, followed by capping the reaction product at all hydroxy locations using tolylene diisocyanate consisting of about an 80/20 mixture of the 2,4 isomer to 2,6 isomer; and in a second step reacting 100 parts by weight of prepolymer with 30 parts by weight of water containing 5 parts by weight of a polyoxyalkylene nonionic surfactant. A particular non-ionic surfactant which has been found useful is one commercially available under the tradename Pluronic L-64 from the Wyandotte Chemicals Corporation. Although the above comprise the preferred hydrophilic urethane foam materials, other useful hydrophilic urethane foams are produced by varying the above prepolymer to water ratio, as well as varying the water to surfactant ratio. Polymeric foams which are to be employed in the preparation of a tampon assembly should preferably possess a maximum density of about 2.5 lbs./ft.$^3$, as difficulties arise in the compression and encapsulation of foams whose density exceeds this level.

The above foams may be further modified in accordance with co-pending applications Ser. Nos. 575,356 and 575,348 filed concurrently herewith, and incorporated herein by reference, which disclose the impregnation of said foams with from 10 to 200% of their weight, of a solid, water insoluble release agent which may be, respectively, either an inorganic, solid material, or a colloidal suspension of a solid, organic material. The above release agents function to keep the cell walls of the foam apart while the foam is in a compressed state and thereby enhance their reexpansion in contact with moisture.

The general preparation of the constrained device comprises the compression of the foam followed by insertion in the compressed state into the capsule. Compression of the foam is usually conducted to a reduction of at least about 50% of its original dry volume, and in a preferred embodiment which is useful in tampon manufacture, the foam may be compressed from about less than 25 to about less than 10%. Any conventional type of press or device may be used. This operation may also be in combination with that of placing the compressed foam into the constraining device. As previously discussed, a preferred constraining device for a tampon is a gelatin capsule or cylinder. The foam piece, which measures about 1 × 1 × 2 inches, can be compressed and placed within the capsule in a single step by any of the many known techniques. One useful technique is to have a cylindrical mold of the same interior diameter as that of the capsule or the sidewalls moveable to such a diameter, which cooperates with a ram which axially thrusts into the mold cavity and forces the foam into the capsule.

In the instance where the device is to function as a tampon, a draw string is attached which may be stitched into place at any time, either to the foam before encapsulation, or to the encapsulated tampon itself. Once placed in the capsule, the foam can be stored indefinitely. As discussed earlier, the gelatin capsule readily dissolves upon contact with moisture, and the foam rapidly expands to contact the vaginal periphery.

In accordance with the present invention, and referring to FIG. 1, the device 10 bearing capsule 11, which may be prepared from a variety of non-toxic, soluble film-forming materials, such as gelatin, is shown with perforations comprising slits 12 extending completely through the capsule wall. Slits 12 extend radially outward from a central point on rounded tip portion 13, and then longitudinally rearward along generally cylindrical body portion 14, stopping, in this illustration before reaching necked region 15. Necked region 15 serves to maintain the foam 16, visible between the edges of slits 12, stationary within capsule 11 and facilitates the nesting of the tampon on the insertion tubes which may be employed, if desired, and are discussed with reference to FIG. 5. Necked region 15 may either be formed by the application of heat and pressure subsequent to the encapsulation of the foam or may be incorporated into the initial shape of the capsule.

Referring further to FIG. 1, slits 12, like necked region 15, may be provided either before or after the encapsulation of foam 16. Thus, the capsule 11 could be formed with slits 12 already disposed therein or, in a preferred embodiment, the slits could be made after insertion and securement of foam 16 within capsule 11, by, for example, passing the encapsulated article between a plurality of radially disposed, radially reciprocable cutting edges or the like, not shown, which may operate by thermal or sonic energy. The particular slitting apparatus may be chosen from such equipment as is presently commercially available. In this illustration, the device, herein tampon 10 is completed and may be packaged and stored until use.

As noted earlier, the devices of the present invention are of such structural integrity that they can maintain their compressed condition throughout extended shelf storage. The fact that the slits 12 extend along a substantial portion of the body portion 14 of capsule 11 without detracting from its strength, comprises one of the surprising and unexpected aspects of this invention. Tampons prepared with slitted capsules can endure months of shelf storage without capsule collapse or disfigurement.

Figure 2:
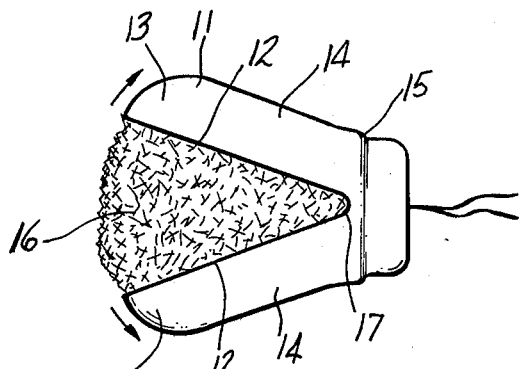
FIG. 2 is a side view showing the device of FIG. 1 at the start of escape and expansion of the foam segment.

In addition to their storage stability, the catamenial devices of the present invention possess the primary advantage of hastening the reexpansion of the compressed foam segment upon its contact with moisture. Turning to FIG. 2, the tampon of FIG. 1 can be seen at the commencement of expansion such as occurs in contact with moisture. Capsule 11 has softened and is being forced open along slit 12 by the expansion of foam 16. Due to the placement of slits 12, capsule 11 exhibits a blossoming effect with expansion being greatest at the top portion 13 and flexion of the capsule wall occuring at the location on the body portion 14 corresponding with the ends 17 of the slits 12. Escape of the foam is swift, and the tampon immediately assumes its position in the vaginal canal. The fully expanded capsule has been shed and has dissolved in the menstruum leaving the foam unhindered in its absorbtive function.

Figure 3:
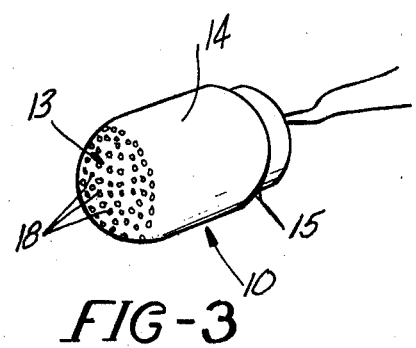
FIG. 3 is a perspective view illustrating an alternate embodiment of the invention.

As noted earlier, the perforations of the present invention may, in an alternate embodiment, comprise a plurality of pin holes uniformly located in the tip area of the capsule. Referring now to FIG. 3, a capsule 10 is depicted which possesses a plurality of such pin holes 18 disposed on tip portion 13. Pin holes, like slits 12, may be provided during the molding of the capsule, or after the securement of the foam within the capsule. The hole forming could be accomplished simply by directing tip portion 13 against the appropriate number of pins fixedly mounted within a cylindrical cavity, or by holding the capsule firmly by body portion 14 and lowering a plunger-like instrument bearing the pins on its leading surface. Naturally, the above techniques are merely representative of a variety of possible ways in which the pin holes 18 may be provided, and the invention should not be construed as limited thereto.

Pin holes 18, like slits 12, provide the foam with increased initial surface contact with moisture which hastens foam expansion. Correspondingly, the tip portion 13 of the capsule tends to disintegrate quickly with the result that the foam is afforded swift direct contact with the menstrual flow.

Though the present invention has been described with reference to a particular capsule configuration, it is intended that variations in overall capsule shape are possible which are fairly within its scope. Thus, FIG. 4 discloses a capsule provided with slits 12′ which varies in configuration from the capsule of FIGS. 1–3. Specifically, the difference resides in the placement of necked region 15′ proximally adjacent tip portion 13′, rather than distally removed therefrom. In this embodiment, body portion 14′ is reduced in diameter over substantially its entire longitudinal dimension, and capsule 11′ resembles a mushroom in shape. As will be seen with reference to FIG. 5, the increased length of body portion 14′ permits capsule 11′ to nest deeply in an insertion device.

Figure 4:
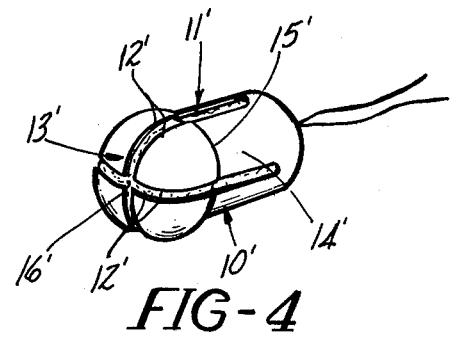
FIG. 4 is a perspective view of a tampon possessing a variant configuration from the tampon of FIG. 1.
Figure 5:
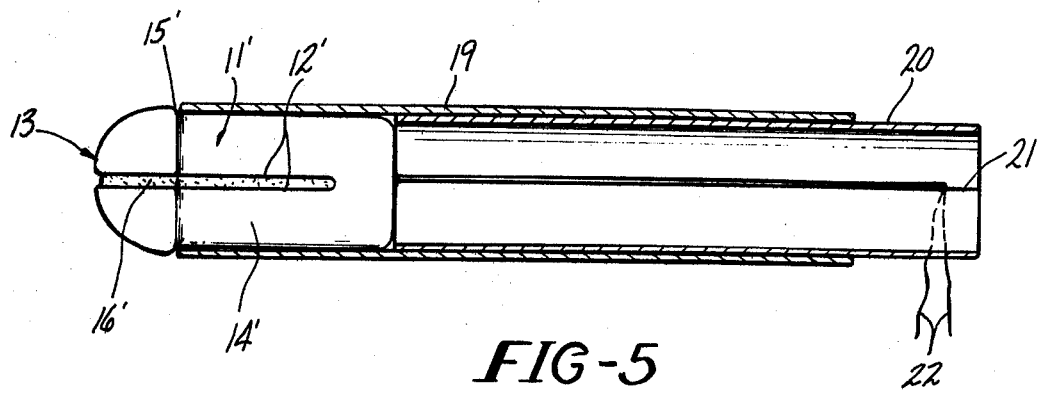
FIG. 5 is a side view partly in section showing the tampon of FIG. 4 mounted on telescoping insertion tubes.

Turning now to FIG. 5, the tampon of FIG. 4 is shown in full assembly prior to insertion, and is mounted on an insertion device comprising two telescoping tubes. Capsule 11′ is mounted within outer tube 19 which firmly grips necked region 15′ and prevents accidental discharge of the tampon. Tube 20 is an ejecting tube which discharges the tampon into the vagina, and is provided at its opposite end thereof with a notch 21 longitudinally extending a short distance which serves to frictionally engage the ends 22 of the withdrawal string and thereby maintain the tampon in fixed position. These tubes may be made from a variety of materials well known for this utility in the tampon art, such as cardboard, plastic, a combination of these materials and the like.

The tampons described above may be employed as prepared or may also contain, as desired, various suitable additives such as disinfectants, perfumes, medicaments, deodorants, emollients, pigments and/or dyes. In a further embodiment, the devices of the present invention may be employed to test for the presence of various microorganisms, by the incorporation of suitable chemical indicators. Naturally, the size and shape of the tampons of this invention may vary widely to account for variations in locus of use and function.

Throughout the specification, all percentages of ingredients are expressed as percent by weight.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A catamenial device comprising:
   a segment of hydrophilic polymeric foam which is held in mechanical compression to less than 50 percent of its original dry volume said segment capable of re-expansion in the dry state; and
   an external, self-sustaining, water-soluble container within which said segment is placed subsequent to the imposition thereon of said mechanical compression, said container serving to substantially hold said segment in said compression therewithin along the entire length of said segment, provides lubrication for insertion of said segment into an animal's body cavity and is adapted for rapid disintegration into said body cavity by the provision of a plurality of perforations in the outer surface thereof.

2. The device of claim 1 wherein said compressed hydrophilic foam comprises a polyurethane foam.

3. The device of claim 1 wherein said compression ranges from about less than 25 percent to about less than 10 percent of said original dry volume.

4. The device of claim 1 wherein said water soluble container comprises a capsule open at one end.

5. The device of claim 4 wherein said perforations comprise radially intersecting slits originating at the closed end of said capsule, and longitudinally extending substantially the major length thereof.

6. The device of claim 4 wherein said perforations comprise a plurality of pin holes uniformly dispersed about the closed end of said capsule.

7. The device of claim 4 wherein said capsule includes a segment adjacent said open end of reduced diameter defining a shoulder about the periphery of said capsule intermediate its ends.

8. The device of claim 7 further comprising removable insertion means axially communicating with said capsule to insert said segment into said body cavity.

9. The device of claim 8 wherein said removable insertion means comprises at least one tube member and said capsule housing said segment is fitted within one end of said tube member with said shoulder abutting thereon.

10. The device of claim 1 further including a withdrawal string affixed to said segment to facilitate removal from said body cavity after use.

11. The device of claim 1 further containing an additive selected from the group consisting of deodorants, disinfectants, perfumes, emollients, medicaments, pigments, dyes and mixtures thereof.

* * * * *